United States Patent [19]

Brown et al.

[11] Patent Number: 4,511,272
[45] Date of Patent: Apr. 16, 1985

[54] WRITING PROSTHESIS

[75] Inventors: Jason W. Brown, 63 Park Ave., Bronxville, N.Y. 10708; Mitchell N. Ackerman, Providence, R.I.

[73] Assignee: Jason W. Brown, Bronxville, N.Y.

[21] Appl. No.: 495,086

[22] Filed: May 16, 1983

[51] Int. Cl.$^3$ .............................................. B43K 29/00
[52] U.S. Cl. .......................................... 401/6; 401/48; 3/12.8
[58] Field of Search ......................... 401/48, 6; 3/12.8

[56] References Cited

U.S. PATENT DOCUMENTS

| 338,239 | 3/1886 | Wyche | 15/437 |
| 478,787 | 7/1892 | Croon | 15/437 X |
| 724,687 | 4/1903 | Floren | 401/48 |
| 1,197,289 | 9/1916 | Henry | 15/443 |
| 1,336,432 | 4/1920 | Henry | 15/437 |
| 2,394,452 | 2/1946 | Howard | 401/48 |
| 2,497,418 | 2/1950 | Schroeder, Jr. | 401/48 |
| 2,748,474 | 6/1956 | Brown | 401/6 X |
| 2,785,462 | 3/1957 | Barg | 401/6 |
| 3,526,006 | 9/1970 | Beardmore | 3/12.8 X |
| 4,095,906 | 6/1978 | Sackett | 401/48 |
| 4,111,566 | 9/1978 | Kenwell | 401/48 X |

FOREIGN PATENT DOCUMENTS

| 76124 | 4/1919 | Austria | 401/48 |
| 459255 | 9/1950 | Italy | 3/12.8 |

Primary Examiner—Steven A. Bratlie

[57] ABSTRACT

A writing prosthesis includes a base adapted to be secured to the forearm of the user and includes a transparent extending portion to which a writing implement may be mounted. The base is supported for universal movement relative to a surface to be inscribed upon.

14 Claims, 5 Drawing Figures

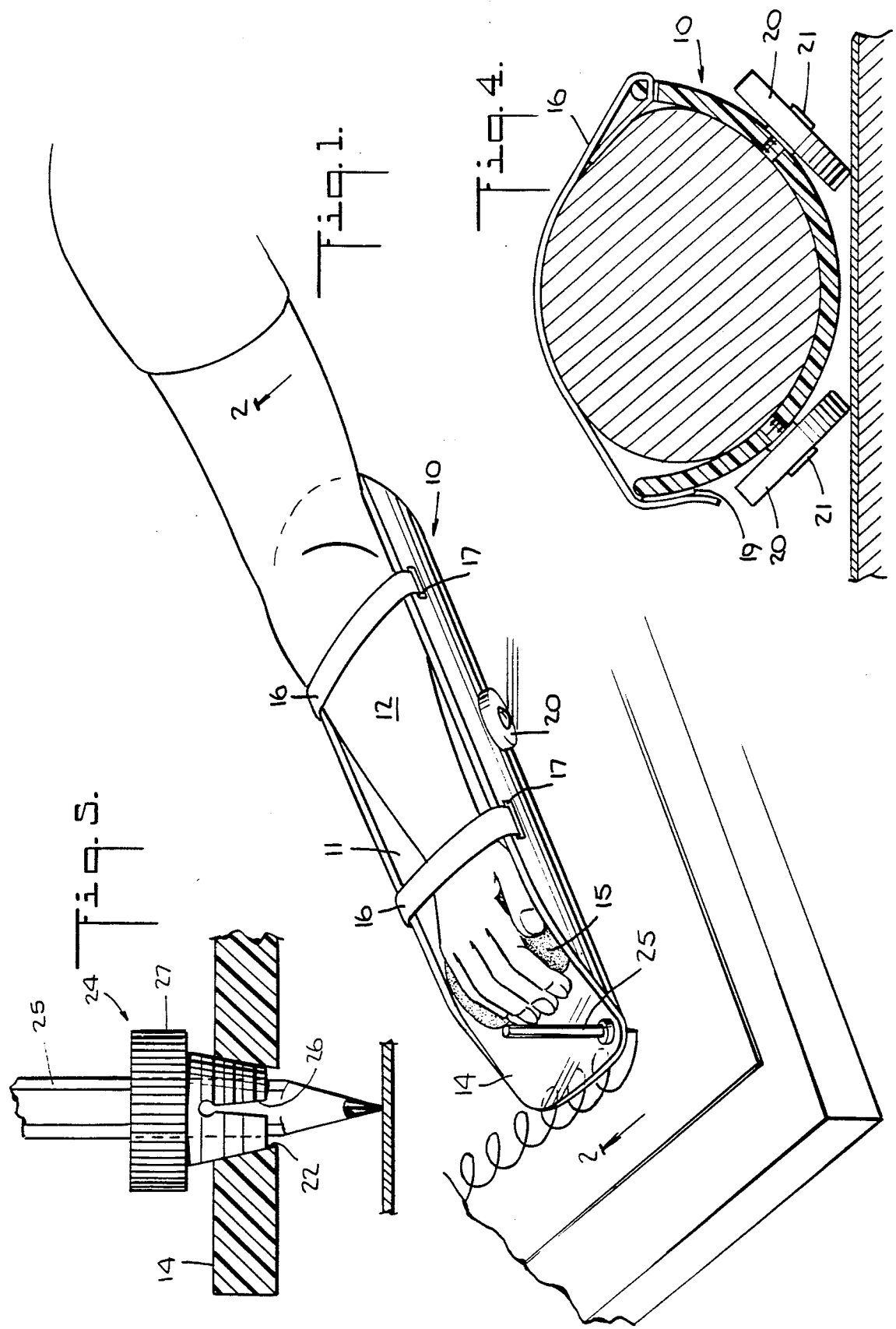

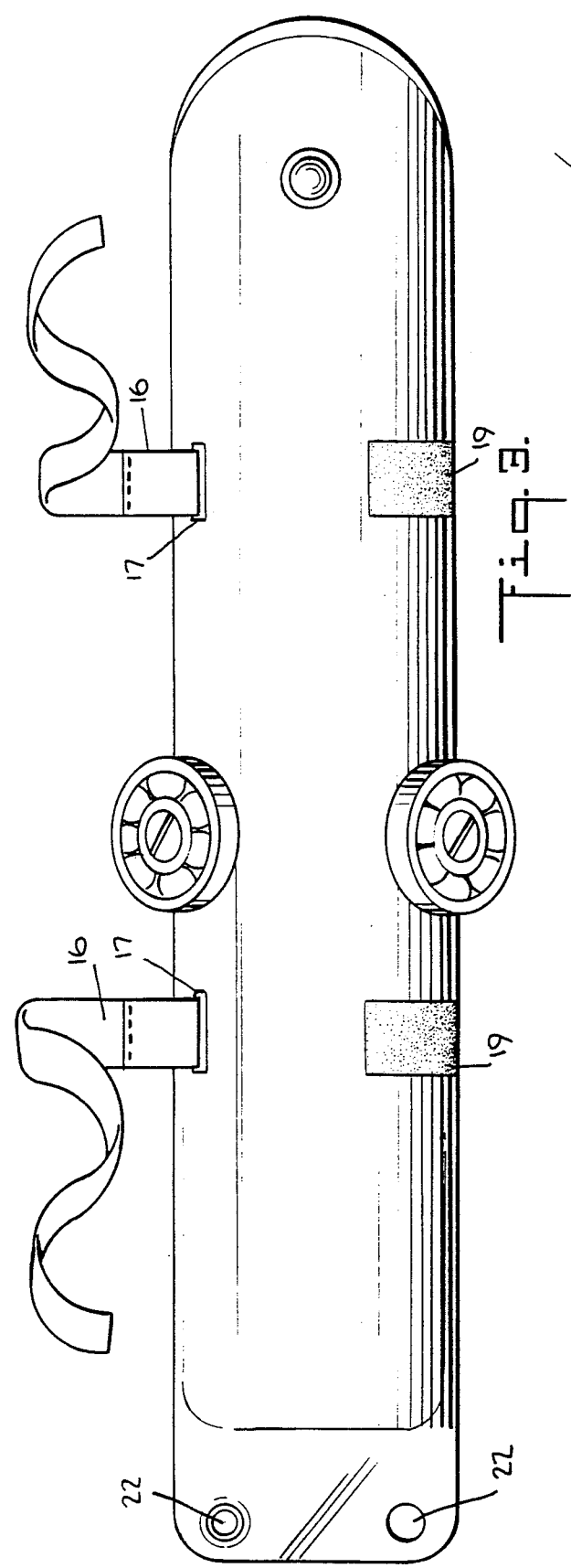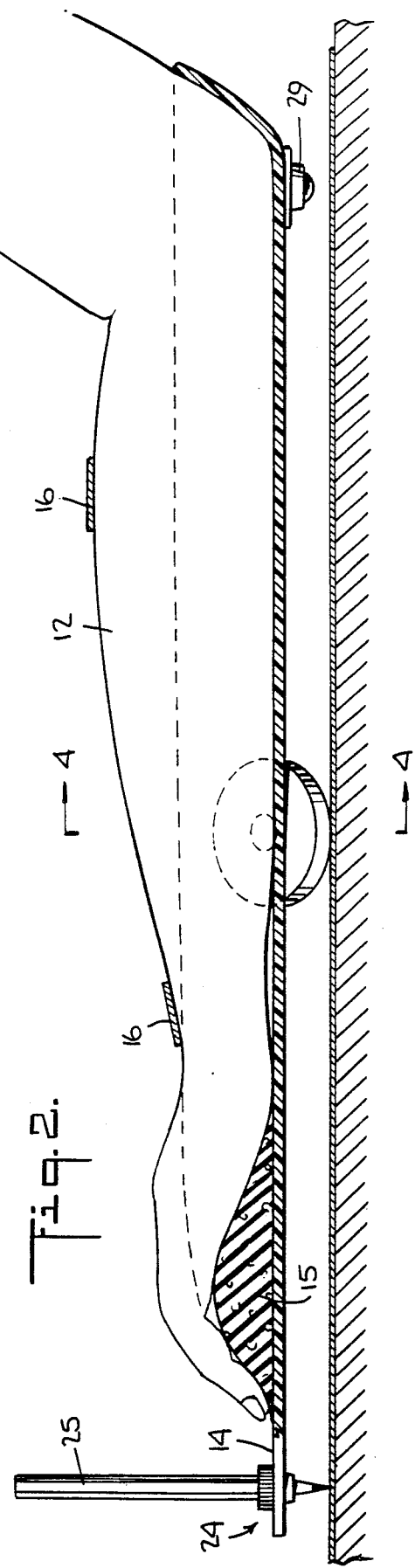

WRITING PROSTHESIS

BACKGROUND OF THE INVENTION

1. Field of the Invention

The present invention relates to a prosthetic device, and more particularly to a writing prosthesis useful to provide a means of communication for individuals suffering paralysis of the arm and hand.

It is known that even in mild aphasics, left-sided agraphia is not unusual; what is unusual is the occasional non-hemiplegic aphasic with left-sided agraphia and a moderate preservation of writing ability on the right side.

Some years ago, Leichner demonstrated hemiplegic writing in global aphasia. Using a plastic ball and pen holder in the rigid right hand, the patient made thrusting movements in the forward and backward directions, the hand being repositioned by the examiner for each succeeding stroke.

In 1983 Brown et al. conducted a study of manual asymmetries in graphic and motor performance in aphasics and designed an apparatus which could be moved easily in all directions. The arm was strapped to the device and it was found that the arm and the device could be moved en bloc by the residual proximal minsuclature without assistance from the examiner. This study has demonstrated that severe aphasics, otherwise unable to communicate in speech or with the left hand, may be able to write with the hemiplegic limb with the aid of a prosthesis. As far as we are aware, this demonstration represents a new approach to treatment in aphasia. Thus, not only may severe aphasics retain the ability to write with the hemiplegic limb, but there is seen the possibility that preliminary, subconsious or pre-processing stages in language can be tapped as a means of facilitating communication in aphasia.

2. Description of the Prior Art

There are several previously known devices for assisting in the writing function to facilitate the same or to improve penmanship. Thus, for example, U.S. Pat. No. 2,748,474 is directed to a scribing device having a hand grip mounted on a base which supports a lens and a guard member formed of tinted plastic to minimize eye strain as the operator moves the device on three anti-friction bearings to scribe a surface by shifting a stylus fixed to the device.

U.S. Pat. No. 478,787 discloses a support for writing instruments which comprises a sleeve for holding the instrument and to which is attached a wire formed with a coil or ring to engage the end of a finger of the user. A cup is attached to the coil for containing a ball adapted to contact the writing surface to reduce friction as writing is effected.

A hand splint for use by persons suffering paralysis of the hand is disclosed in U.S. Pat. No. 3,526,006. A person in need of this device can raise his hand at the wrist but cannot press down and the arrangement is such that the force of a resilient member can be overcome by the user's wrist action to open opposed jaws of the device while the resilient force is relied upon for grasping action.

Other patents of interest are U.S. Pat. Nos. 1,197,289, 1,336,432 for writing aids, U.S. Pat. No. 338,239 for a hand suport for use when writing U.S. Pat. No. 2,755,772 for a device for attaching to the arm a writing instrument container including retracting means for the instrument, and U.S. Pat. No. 2,785,462 for a head supported scribing instrument. None of the aforementioned patents offer a solution of the problem discussed above and which we have attacked and solved.

SUMMARY OF THE INVENTION

We have conceived and contribute by the present invention a writing prosthesis useful for written communication by hemiplegic aphasics; and we have actually constructed and successfully tested a commercially desirable prosthesis based upon that concept.

Thus, according to one aspect of my invention, we provide a base adapted to engage, and to be secured to, the forearm of the user and having a portion thereof extending beyond the distal ends of the fingers, the base being provided with a handrest contoured to engage the palm and fingers of the user. A writing implement such as a pen or pencil may be secured to the extending portion of the device by appropriate mounting means for writing contact with an adjacent writing surface to be inscribed upon, and means are provided for supporting the device for universal movement relative to that surface. Thus, the prothesis may be controlled by the residual proximal muscles of the user to cause the writing implement to inscribe intelligent indicia on the writing surface.

The base is preferably elongate and semi-tubular in lateral cross-section to engage the full length of the underside of the forearm and may be formed with an upstanding wall at the end opposite the extending portion to engage the rear surface of the elbow.

As stated, the base is adapted to be secured to the forearm. To this end we provide means in the form of a pair of straps, each fixed at one end to the base and arranged to extend across the forearm and to be secured at the other end to the base as by suitable snaps, velcro strips, or the like.

To enable universal movement of the prosthesis relative to a writing surface, we provide two rotatable means mounted to the base each to contact the writing surface at a point offset laterally of the vertical central plane of the base to prevent rolling movement of the forearm about its longitudinal axis. More specifically, the rotatable means may take the form of wheels mounted one on each side of the base and rotable about axes intersecting a longitudinal axis of the base at an angle of the order of about 45°. In lieu of wheels, we may use circular anti-friction rollers or casters.

To permit the user to separate the writing implement from the writing surface without lifting the entire prosthesis, we provide a depending element at the end of the base opposite the extending portion to depend a distance less that than between the base and the writing surface when the writing instrument is in contact with the writing surface, the base and writing surface being substantially parallel at that time. The depending element may be constituted by an anti-friction roller so that the user may rock or pitch the elbow downwardly to bring the depending element into contact with the surface thus lifting the writing implement from the surface, in which position the device can readily be moved to position it to start a new character.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which this disclosure is based may readily be utilized as a basis for the designing of other structures for carrying out the several purposes of the invention. It is important, therefore, that the claims be regarded as including such equivalent constructions as do not depart from the spirit and scope of the invention.

BRIEF DESCRIPTION OF THE DRAWINGS

Specific embodiments of the invention have been chosen for purposes of illustration and description, and are shown in the accompanying drawings, forming a part of the specification wherein:

FIG. 1 is a perspective view of a prosthetic device according to the present invention attached to the arm of a user and in the act of writing;

FIG. 2 is a cross-sectional view taken along the line 2—2 of FIG. 1;

FIG. 3 is the bottom view of the device;

FIG. 4 is a cross-sectional view taken along the line 4—4 of FIG. 2; and

FIG. 5 is a detail view, partly in section, illustrating a writing implement mounted in the extending portion of the device.

DESCRIPTION OF THE PREFERRED EMBODIMENT

Referring now to the drawing, and especially to FIGS. 1 and 2 thereof, there is shown a writing prosthesis comprising an elongate base 10 of semi-tubular cross-section to provide a grooved arm rest 11 in which the forearm 12 of a user may comfortably rest. The sides of the base 10 taper downwardly at the forward end (the left end, as viewed) and merge with a transparent flat portion 14 that extends beyond the distal ends of the user's fingers and a raised pad 15, contoured to engage the palm and fingers, is provided in the groove of the base to constitute a handrest. The rear of the base is closed by a curved section to engage the rear surface of the elbow of the user.

As best shown in FIGS. 1, 3 and 4, means in the form of a pair of straps 16 are provided to secure the forearm 12 to the base 10. To this end, we form a pair of spaced apart slots 17 in one sidewall of the base 10, and pass a strap through each slot so that each strap may be folded back and secured upon itself. The other end of each strap may then be secured as by velcro strips 19 to the opposite side of the base 10. As shown in FIG. 1, we prefer that one strap pass over the user's wrist while the other is arranged to cross the upper portion of the forearm.

The base 10 is supported for universal movement relative to the surface upon which it rests by rotable means mounted on the base to contact the surface at points offset laterally of the vertical plane of the base. The rotatable means are shown in FIGS. 1 to 4 as a pair of wheels rotable about axles 21 studded in the base so that the axes of rotation of the wheels intersect the longitudinal axis of the base at an angle of the order of about 45° as viewed in FIG. 4. The treads of the wheels are preferably flat, as shown, to assure point contact with the underlying surface against which they bear. It will be appreciated that anti-friction bearings or caster mounted wheels may be used in lieu of those wheels illustrated.

As shown in FIGS. 3 and 5, the flat extending portion 14 at the forward end of the base 10 is provided with one or more tapered holes 22 for threadedly receiving a clamp 24. This clamp is adapted to support a writing implement or stylus 25 for point contact with a surface to be inscribed and for this purpose, it is formed with a keyhole slot 26 extending from its lower end, as viewed, so that, as it is threaded into an opening 22, its clamping force on the writing implement is increased. The upper end of the clamp 24 may be formed with a knurled collar 27 to facilitate insertion of the clamp into the opening.

FIGS. 3 and 4 illustrate a depending element 29 provided at the rear end of the base to depend a distance from the base less than the distance between the base and the writing surface when the writing implement 25 is properly mounted and in contact with the writing surface, in which condition the longitudinal axis of the base is substantially parallel with the plane of the writing surface. The depending element 29 preferably takes the form of an anti-friction spherical roller.

In use, the base 10 is strapped to the forearm of an aphasic, as in FIGS. 1 and 2, and a writing implement 25 is mounted in one of the openings 22 to depend from the extending portion 14 of the base for contact with a writing surface when the longitudinal axis of the base is substantially parallel with the plane of the surface while the rotatable means 20 rest on the surface. We have found that, with the device so affixed to the forearm, aphasics can employ the residual proximal muscles to execute controlled movement of the prosthesis, and thus the writing implement, to inscribe intellegent indicia on the writing surface which surface can be viewed by the user due to the transparency of the extending portion 14. To separate indicia, the prosthesis can be pivoted about the rotable means 20 to lower the depending element 29 to the surface thus raising the writing implement from the surface, so that the writing implement can be shifted to the next starting point.

We believe that the construction and operation of our novel prosthesis will now be understood and that the advantages thereof will be fully appreciated by those persons skilled in the art.

We claim:

1. A writing prosthesis comprising:
 a base adapted to engage and to support the entire forearm and the elbow of a user and having a forward portion extending beyond the distal ends of the fingers of the user;
 means for securing said base to the forearm;
 a handrest mounted on said base and contoured to engage the palm and fingers;
 mounting means for removably securing a writing implement to said forward portion of said base for writing contact with an adjacent writing surface to be inscribed upon; and
 rotatable support means connected to the base for supporting the writing instrument and the forearm for universal movement relative to said surface;
 whereby, the prosthesis and the forearm may be controlled solely by the shoulder muscles of the user to cause the writing implement to inscribe intelligent indicia on said surface.

2. A writing prosthesis according to claim 1, wherein said base is elongate and semi-tubular in lateral cross-section.

3. A writing prosthesis according to claim 1 or 2, wherein said base is formed with a raised portion adapted to engage the rear surface of the elbow.

4. A writing prosthesis according to claim 1, wherein said securing means comprise a pair of straps, each fixed at one end to said base and adapted to extend across the forearm and to be secured at the other end to the base.

5. A writing prosthesis comprising:
an elongated base having a semi-tubular lateral cross-section, adapted to engage and to support the entire forearm and the elbow of a user, and having
(i) a forward portion extending beyond the distal ends of the fingers of the user, and
(ii) a raised back portion adapted to engage the rear surface of the elbow;
means for securing said base to the forearm;
a handrest mounted on said base and contoured to engage the palm and fingers of the user;
mounting means for removably securing a writing implement to said forward portion of said base for writing contact with an adjacent surface to be inscribed upon; and
rotatable support means mounted to said base to contact said surface at points offset laterally of the vertical central plane of said base to support the base, the writing instrument, and the forearm for universal movement relative to said surface;
whereby, the prosthesis and the forearm may be controlled solely by the shoulder muscles of the user to cause the writing implement to inscribe intelligent indicia on said surface.

6. A writing prosthesis according to claim 5, wherein said rotatable means comprise first and second wheels mounted to said base on different sides of the vertical central plane thereof.

7. A writing prosthesis according to claim 6, wherein said first and second wheels are rotatable about axes intersecting a longitudinal axis of said base at an angle of the order of about 45°.

8. A writing prosthesis according to claim 5, wherein said rotatable means comprise anti-friction rollers.

9. A writing prosthesis according to claim 5, wherein said rotatable means comprise caster mounted wheels.

10. A writing prosthesis according to claim 1 or 5 wherein a depending element is provided at the end of said base opposite said forward portion to depend a distance less than the distance between said body and the surface to be inscribed upon when the writing implement is in contact with the surface.

11. A writing prosthesis according to claim 10, wherein said depending element is an anti-friction roller.

12. A writing prosthesis according to claim 5, wherein said mounting means comprises a tapered hole formed in said forward portion and an apertured slotted clamp threadably engageable in said hole to secure a writing implement extending through the aperture to said forward portion.

13. A writing prosthesis according to claim 1 or 5, wherein said forward portion is transparent.

14. A writing prosthesis according to claims 2 or 5 wherein:
said forward portion of the base is generally flat; and
the sides of the base taper downwardly at a front end of the base.

* * * * *